United States Patent [19]

Grandadam

[11] Patent Number: 4,900,735

[45] Date of Patent: Feb. 13, 1990

[54] ZOOTECHNICAL COMPOSITIONS

[75] Inventor: Jean A. Grandadam, Saint-Maur Des Fosses, France

[73] Assignee: Roussel Uclaf, Paris, France

[21] Appl. No.: 131,729

[22] Filed: Dec. 11, 1987

[30] Foreign Application Priority Data

Dec. 11, 1986 [FR] France .............................. 86 17334
Aug. 13, 1987 [FR] France .............................. 87 11543
Aug. 13, 1987 [FR] France .............................. 87 11542

[51] Int. Cl.$^4$ ................................................ A61K 31/56
[52] U.S. Cl. .................................... 514/171; 514/387; 514/731
[58] Field of Search .................. 514/171, 387, 731

[56] References Cited

U.S. PATENT DOCUMENTS

| | | | |
|---|---|---|---|
| 3,248,294 | 4/1966 | Nomine et al. | 260/397.3 |
| 3,885,047 | 5/1975 | Seidehamel et al. | 514/597 |
| 3,939,265 | 2/1976 | Grandadam | 260/397.5 |
| 3,989,828 | 11/1976 | Aries | 514/171 |
| 4,404,224 | 9/1983 | Asato | 564/99 |
| 4,407,819 | 10/1983 | Kiernan et al. | 514/524 |
| 4,477,680 | 10/1984 | Asato | 564/82 |
| 4,618,624 | 10/1986 | Asato | 514/486 |
| 4,761,421 | 8/1988 | Muir | 514/352 |

FOREIGN PATENT DOCUMENTS 2534257 of 1982 France .
2192133 1/1988 United Kingdom .

OTHER PUBLICATIONS

"Derivatives of 6-Amino-7-Hydroxy $\alpha$,5,6,7-Tetrahydroimidazo [4,5,1-JK][1]Benzazepin-2(1H)-one", Frechet et al., 1982, Chem. Abst., vol. 101; 151846.

Primary Examiner—H. M. S. Sneed
Assistant Examiner—J. Saba
Attorney, Agent, or Firm—Bierman and Muserlian

[57] ABSTRACT

A zootechnical association comprising (a) a zootechnical composition containing a beta adrenergic and (b) a zootechnical composition containing a steroid of the formula

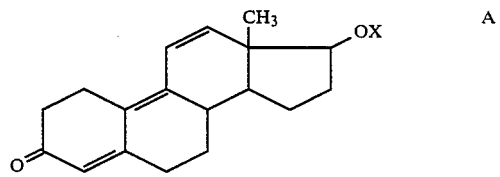

wherein X is selected from the group consisting of hydrogen, optionally unsaturated alkyl of 1 to 6 carbon atoms wherein one of the carbon atoms may be replaced by —O— and acyl of an organic carboxylic acid of 1 to 18 carbon atoms and a method increasing the weight and quality of meat of animals by administration simultaneously, separately or spread out over a period of time.

24 Claims, No Drawings

ZOOTECHNICAL COMPOSITIONS

STATE OF THE ART

Relevant prior art includes U.S. Pat. Nos. 4,192,870 and 4,585,770 and French Patents No. 2,238,476 and No. 2,230,378.

OBJECTS OF THE INVENTION

It is an object of the invention to provide novel technical compositions comprising a beta adrenergic and a steroid of formula A and a novel method of increasing the weight and quality of meat of warm-blooded animals.

These and other objects and advantges of the invention will become obvious from the following detailed description.

THE INVENTION

The zootechnical compositions of the invention are comprised of (a) a zootechnical composition containing a beta adrenergic and (b) a zootechnical composition containing steroid of the formula

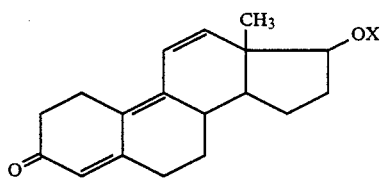

wherein X is selected from the group consisting of hydrogen, optionally unsaturated alkyl of 1 to 6 carbon atoms wherein one of the carbon atoms may be replaced by —O— and acyl of an organic carboxylic acid of 1 to 18 carbon atoms.

Beta adrenergics are well known for use in human medicine and certain beta adrenergics are described as having anabolisant activity in animals such as German Patent No. 3,234,995 and European Patent No. 103,830. Applicants have surprisingly found that particularly interesting results are obtained by the association of beta adrenergics with a steroid of formula A as the association results in a remarkable increase in the weight and quality of the meat of the animals such as bovines, pigs, sheep and fowl. The effect of the said association is much superior to the effect obtained by administering the same beta adrenergic alone or the same steroid alone.

The compounds of formula A are known products described, for example, in French Patents No. 1,380,414 and No. 1,492,985 as well as Belgium Patent No. 696,084. The preferred compound of formula A is 11β-acetoxy-$\Delta^{4,9,11}$-estratriene-3-one.

Among the preferred associations of the invention are the compositions where the steroid of formula A is trenbolone acetate or 17β-acetoxy-$\Delta^{4,9,11}$-estratriene-3-one and the beta adrenergic is at least one compound of the formula

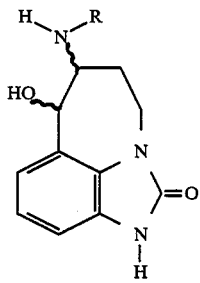

wherein R is selected from the group consisting of hydrogen, cycloalkyl of 3 to 7 carbon atoms, piperidinyl with the nitrogen optionally substituted by alkyl of 1 to 4 carbon atoms and alkyl of 1 to 8 carbon atoms optionally substituted by —OH or phenyl or phenoxy and the wavy lines indicate that the 7-OH and 6-NH$_2$ have the trans configuration and their non-toxic, pharmaceutically acceptable acid addition salts.

In the compounds of formula I, R may be alkyl of 1 to 8 carbon atoms such as n-pentyl, n-butyl, n-propyl, 2,2-dimethylpropyl and preferably methyl, ethyl and isopropyl; cycloalkyl of 3 to 7 carbon atoms such as cyclopropyl, cyclobutyl, cyclopentyl, cyclohexyl and cycloheptyl.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and aryl carboxylic acids such as benzoic acid.

The compounds of formula I are compounds known for their anti-hypertensive and hypotensive activity as can be seen from European Patent No. 107,569.

Among the preferred associations of the invention are those where the compounds of formula I have R as hydrogen or alkyl of 1 to 5 carbon atoms and their non-toxic, pharmaceutically acceptable addition salts and those wherein the beta adrenergic is (6RS, trans) 6-isopropylamino-7-hydroxy-4,5,6,7-tetrahydroimidazo[5,4,1-j-k]benzazepine-2(1H)-one and its non-toxic, pharmaceutically acceptable acid addition salts, especially its hydrochloride.

Other preferred associations of the invention are those wherein the beta adrenergic is salbutamol of the formula

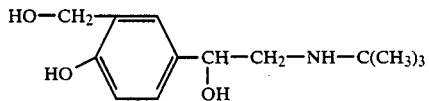

Salbutamol is a known compound and salbutamol or albuterol is α-[tert.butylamino methyl]-4-hydroxy-n-xylene-α,α'diol are known for their activity on beta-2 receptors of bronchial smooth muscles and is sold for the treatment of asthma.

Other useful beta adrenergics are cimaterol of the formula

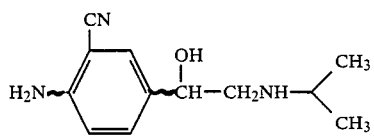

and clembuterol of the formula

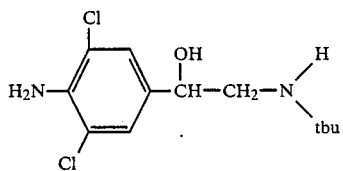

as well as the compounds described in German patent No. 3,234,995 and European patent No. 103,830.

In a preferred embodiment of the invention, the association includes besides, (a) a zootechnical composition containing a beta adrenergic of formula I and (b) a zootechnical composition containing a steroid of formula A, (c) a zootechnical composition containing zeranol or estradiol which components may be administered separately, simultaneously or spread out over a period of time.

Remarkable results are obtained when the product of formula I is (6RS, trans) 6-isopropylamino-7-hydroxy-4,5,6,7-tetrahydroimidazo[5,4,1-j-k]benzazepin-2-(1H)-one and its non-toxic, pharmaceutically acceptable acid addition salts and the compound of formula A is 17β-acetoxy-$\Delta^{4,9,11}$-estratriene-3-one.

Other preferred associations of the invention are (a) a zootechnical composition containing salbutamol, (b) a zootechnical composition containing trenbolone acetate and (c) a zootechnical composition containing either zeranol or estradiol which components may be administered separately, simultaneously or at different periods of time.

Another embodiment of the invention comprises an association of (a) zootechnical composition containing a compound of formula I, (b) a zootechnical composition containing ($b_1$) a compound of formula A and ($b_2$) zeranol or estradiol which may be administered simultaneously, separately or spread out over a period of time. Especially preferred are compositions of (a) a zootechnical composition containing (6RS, trans) 6-isopropylamino-7-hydroxy-4,5,6,7-tetrahydroimidazo[5,4,1-j-k]benzazepin-2-(1H)-one or its non-toxic, pharmaceutically acceptable acid addition salts and (b) a zootechnical composition containing ($b_1$) trenbolone acetate and ($b_2$) zeranol.

A preferred association of the invention comprises (a) a zootechnical composition containing salbutamol and (b) a zootechnical composition containing ($b_1$) trenbolo-one acetate and ($b_2$) zeranol or estradiol which can be administered separately, simultaneously or spread out over a period of time.

Zootechnical compositions of the invention are zootechnical compositions containing an effective amount of at least one compound of the formula

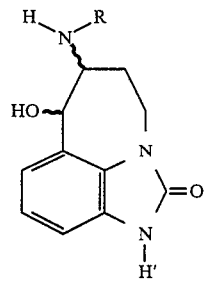

wherein R is selected from the group consisting of hydrogen, cycloalkyl of 3 to 7 carbon atoms, piperidinyl with the nitrogen optionally substituted by alkyl of 1 to 4 carbon atoms and alkyl of 1 to 8 carbon atoms optionally substituted by —OH or phenyl or phenoxy and the wavy lines indicate that the 7-OH and 6-$NH_2$ have the trans configuration and their non-toxic, pharmaceutically acceptable acid addition salts.

In the compounds of formula I, R may be alkyl of 1 to 8 carbon atoms such as n-pentyl, n-butyl, n-propyl, 2,2-dimethylpropyl and preferably methyl, ethyl and isopropyl; cycloalkyl of 3 to 7 carbon atoms such as cyclopropyl, cyclobutyl, cyclopentyl, cyclohexyl and cycloheptyl.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and aryl carboxylic acids such as benzoic acid.

Among the preferred zootechnical associations of the invention are those where the compounds of formula I have R as hydrogen or alkyl of 1 to 5 carbon atoms and their non-toxic, pharmaceutically acceptable addition salts and those wherein the beta adrenergic is (6RS, trans) 6-isopropylamino-7-hydroxy-4,5,6,7-tetrahydroimidazo[5,4,1-j-k]benzazpin-2-(1H)-one and its non-toxic, pharmaceutically acceptable acid addition salts, especially its hydrochloride.

Among the preferred zootechnical compositions are also those which contain salbutamol as the active ingredient.

The associations and zootechnical compositions of the invention increase the weight and improve the quality of the meat of slaughter animals such as bovines, sheep, especially lambs, pigs and calves as well as for fowl.

The beta adrenergics are preferably administered to the animals orally in the form of tablets, granules or powders incorporated into the feed for pigs or calves prepared by the known procedures of such products but they may also be administered parenterally.

The feed mixture will vary depending on the animal species but usually contains cereals, sugars, grains, arachidic and tournsole and soybean press cake, flours of animal origin such as fish flour, amino acids of synthesis, mineral salts, vitamins and antioxidants.

For administration to cattle, the product of formula A as well as zeranol or estradiol can be administered in the form of an implant behind the ear or baleen. It may be implanted 20 days to four months, preferably 1 to 3 months, before slaughter. The product of Formula A, zeranol and estradiol can also be administered by injection as a solution or suspension or orally with feed.

The compositions and associations of the invention manifest interesting anabolisant properties, particularly protidic anabolisant properties. They are useful with veterinary medications, especially to increase the general organic resistance to agressions of all sorts, to combat loss of weight, emaciation, general organic problems due to old age and to combat secondary effects of infectious, parasitic and nutritional maladies.

The novel method of improving meat quality and weight in slaughter animals comprises administering to slaughter animals an effective amount of a zootechnical composition or association of the invention as discussed above. The administration may be oral or parenteral and the daily dose will depend on the specific compounds, the method of administration and the animal being treated. The beta adrenergic is usually orally administered at a dose of 10 to 1000 meg/kg or in a zootechnical composition in implant form of 0.5 to 300 mg of the beta adrenergic. Zeranol is usually administered as a zootechnical composition containing 10 to 100 ml of zeranol. Zeranol can be administered as an implant for example. Estradiol is usually administered as a zootechnical composition containing 0.05 to 50 ml of estradiol.

The product of Formula A is usually administered as zootechnical composition containing 1 to 300 mg of product A.

Particularly interesting associations of the method of the invention are those containing 1 to 100 mg of the beta adrenergic, for example, 5 to 25 mg of the beta adrenergic and implants containing 5 to 50 mg of trenbolone acetate or $17\beta$-acetoxy-$\Delta^{4,9,11}$-estratriene-3-one and 10 to 50 mg of zeranol.

In the following examples there are described several preferred embodiments to illustrate the invention. However, it should be understood that the invention is not intended to be limited to the specific embodiments. The Product $P_1$ in the examples is (6RS, trans) 6-isopropylamino-7-hydroxy-4,5,6,7-tetrahydroimidazo[5,4,1-j-k]benzazepin-2-(1H)-one.

EXAMPLE 1

Tablets were prepared containing 5 mg of Product $P_1$ and sufficient excipient of lactose, wheat starch, treated starch, rice starch, talc and magnesium stearate for a final weight of 100 mg.

EXAMPLE 2

Granules were prepared containing 25 mg of Product $P_1$ in each daily dose of granules.

EXAMPLE 3

Associations were prepared consisting of granules containing 25 mg of Product $P_1$ in the daily dose of granules and implant $P_2$ containing 20 mg of trembolone acetate and 36 mg of zeranol.

EXAMPLE 4

Tablets were prepared containing 5 mg of salbutamol and sufficient excipient of lactose, wheat starch, treated starch, rice starch, talc and magnesium stearate for a final weight of 100 mg.

EXAMPLE 5

Granules were prepared containing 25 mg of salbutamol per daily dose of granules.

EXAMPLE 6

Associations were prepared consisting of (a) granules containing 25 mg of salbutamol in the daily dose of granules and (b) implants containing 20 mg of trenbolone and implants containing 36 mg of zeranol.

EXAMPLE 7

This test was effected on pigs divided into four groups wherein one group (1) was the control with nothing in the feed, one group (2) receiving 200 mg/kg of Product $P_1$ per day in the feed, one group (3) receiving 250 mg/kg of Product $P_1$ per day in the feed and having an implant of $P_2$ of Example 3 and one group (4) having the implant $P_2$ of Example 3 and nothing in the feed. The product $P_1$ was incorporated into the feed and the implant $P_2$ was placed in the subcutaneous tissue in the rear of the ear. The animals all received the same feed for 90 days and the results are reported in Table I.

TABLE I

|  | Groups | | | |
| --- | --- | --- | --- | --- |
|  | (1) | (2) | (3) | (4) |
| No. of pigs | 10 | 10 | 10 | 10 |
| Ave. no. of days of fattening | 28 | 28 | 28 | 28 |
| Ave. weight at implantation in Kg | 82.00 | 81.80 | 81.80 | 81.80 |
| Ave. weight at slaughter in Kg | 103.00 | 103.90 | 107.60 | 103.30 |
| Weight gain in Kg | 21.00 | 22.10 | 25.80 | 21.50 |
| Ave. daily weight gain in Kg | 0.750 | 0.789 | 0.921 | 0.768 |

The results of Table I showed that the treated group had a greater weight gain than the control group but the group (3) of the invention had a very exceptional increase superior to the additive effects caused by the separate administration of Product $P_1$ and implant $P_2$.

EXAMPLE 8

This test was effected on pigs divided into four groups: one group (1) received nothing in the feed, one group (2) received 0.25 mg/kg of salbutamol daily in the feed, one group (3) received 0.25 mg/kg of salbutamol daily in the feed and had an implant $P_2$ (as in Example 3) and one group (4) received the implant $P_2$ (as in example 3) and nothing in the feed. Salbutamol was incorporated into the feed and the implant was placed in the subcutaneious tissue behind the ear. All the animals received the same feed for 90 days and the results are reported in Table II.

TABLE II

|  | Controls | | | |
| --- | --- | --- | --- | --- |
| Treatments | (1) | (4) | (3) | (2) |
| Days of treatment before slaughter |  | 54 | 54 | 54 |
| No. of pigs. | 9 | 9 | 9 | 9 |
| Average weight in Kg on day of treatment | 61.67 | 61.67 | 61.67 | 61.56 |
| Average weight in Kg at end of test | 103.22 | 105.67 | 106.22 | 104.44 |
| Average weight gain in Kg | 41.56 | 44.00 | 44.56 | 42.89 |

TABLE II-continued

| | Controls | | | |
|---|---|---|---|---|
| Treatments | (1) | (4) | (3) | (2) |
| Ave daily weight gain in Kg | 0.770 | 0.815 | 0.825 | 0.794 |
| Weight of fresh carcasses in Kg | 80.22 | 82.82 | 84.89 | 82.49 |
| Feed consumed in Kg | 130.17 | 129.79 | 129.21 | 130.02 |
| Index of consummation | 3.14 | 2.96 | 2.92 | 3.05 |

Table II shows that the associations of the invention give very good results in increased weight.

EXAMPLE 9

This test was conducted on male calves divided into two groups with group I receiving no additive to the feed and Group II receiving 0.1 mg/kg of live weight of salbutamol. The tests were run three times with a test period of 85 days, a test period of 34 days and a post experimental period of 15 days. The weights were all determined for 15 days and all the animals received a daily ration of feed throughout the test and the results are reported in Table III.

TABLE III

| Groups | I | II |
|---|---|---|
| No. of calves | 9 | 10 |
| No. of days of fattening | 134 | 134 |
| Ave. weight on day of treatment in Kg | 140.22 | 141.50 |
| Ave. weight in Kg at end of test | 179.00 | 185.40 |
| Ave. weight gain in Kg | 38.78 | 43.90 |
| Ave. daily weight gain in Kg | 1.141 | 1.291 |
| Feed consumed in Kg | 81.90 | 82.00 |
| Consumption index | 2.11 | 1.87 |

EXAMPLE 10

This test was conducted on male and female lambs divided into three groups: group (1) received 0.2 mg/kg of product $P_1$, group (2) received 0.4 mg/kg of product $P_1$ and group (3) was the control group receiving no treatment. Product $P_1$ was incorporated into the feed which was granules in daily quantities and as much hay as they desired. The results showed a clear improvement in weight gain and conformation of the lambs of groups 1 and 2 as compared to control group 3.

Various modifications of the associations and the method of the invention may be made without departing from the spirit or scope thereof and it should be understood that the invention is intended to be limited only as defined in the appended claims.

What I claim is:

1. A zootechnical composition comprising a weight increasing amount of (a) a zootechnical composition containing a beta adrenergic of at least one compound selected from the group consisting of a compound of the formula

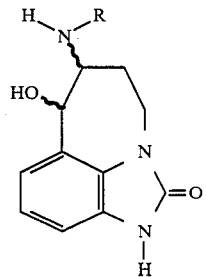

wherein R is selected from the group consisting of hydrogen, cycloalkyl of 3 to 7 carbon atoms, piperidinyl with the nitrogen unsubstituted or substituted by alkyl of 1 to 4 carbon atoms and alkyl of 1 to 8 carbon atoms unsubstituted or substituted by —OH or phenyl or phenoxy and the wavy lines indicate that the 7-OH and 6-NH$_2$ have the trans configuration and their non-toxic, pharmaceutically acceptable acid addition salts and (b) a zootechnical composition containing a steroid of the formula

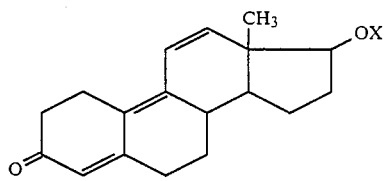

wherein X is selected from the group consisting of hydrogen, alkyl of 1 to 6 carbon atoms wherein one of the carbon atoms may be replaced by —O— and acyl of an organic carboxylic acid of 1 to 18 carbon atoms.

2. An composition of claim 1 wherein the steroid of formula A is trenbolone acetate.

3. An composition of claim 1 wherein R of the compound of formula I is hydrogen or alkyl of 1 to 5 carbon atoms.

4. An composition of claim 1 containing (6RS, trans) 6-isopropylamino-7-hydroxy-4,5,6,7-tetrahydroimidazo[5,4,1-j-k]benzazepin-2-(1H)-one and its non-toxic, pharmaceutically acceptable acid addition salts.

5. An composition of claim 1 also containing (a) a zootechnical composition containing zeranol.

6. An composition of claim 1 also containing (a) a zootechnical composition containing estradiol.

7. An composition of claim 5 wherein the beta adrenergic is selected from the group consisting of (6RS, trans) 6-isopropylamino-7-hydroxy-4,5,6,7-tetrahydroimidazo[5,4,1-j-k]benzazepin-2-(1H)-one and its non-toxic, pharmaceutically acceptable acid addition salts and the compound of formula A is trenbolone acetate.

8. An composition of claim 6 wherein the beta adrenergic is selected from the group consisting of (6RS, trans) 6-isopropylamino-7-hydroxy-4,5,6,7-tetrahydroimidazo[4,5,1,-j-k]benzazepin-2-(1H)-one and its non-toxic, pharmaceutically acceptable acid addition salts and the compound of formula A is trenbolone acetate.

9. An composition of claim 4 wherein the zootechnical composition (b) also contains zeranol.

10. A zootechnical composition comprising a weight increasing effective amount of at least one compound selected from the group consisting of a compound of the formula

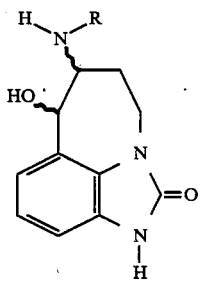

wherein R is selected from the group consisting of hydrogen, cyclyalkyl of 3 to 7 carbon atoms, piperidinyl with the nitrogen unsubstituted or substituted by alkyl of 1 to 4 carbon atoms and alkyl of 1 to 8 carbon atoms unsubstituted or substituted by —OH or phenyl or phenoxy and the wavy lines indicate that the 7-OH and 6-$NH_2$ have the trans configuration and their non-toxic, pharmaceutically acceptable acid addition salts and an inert carrier.

11. A composition of claim 10 wherein R is hydrogen or alkyl of 1 to 5 carbon atoms.

12. A composition of claim 10 wherein the active compound is selected from the group consisting of (6RS, trans) 6-isopropylamino-7-hydroxy-4,5,6,7-tetrahydroimidazo[5,4,1-j-k]benzazepin-2-(1H)-one and its non-toxic, pharmaceutically acceptable acid addition salts.

13. A method of increasing the weight of pigs comprising administering to pigs a weight increasing effective amount of an composition of claim 1.

14. A method of increasing the weight of calves comprising administering to calves a weight increasing effective amount of an composition of claim 1.

15. A method of increasing the weight of pigs comprising administering to pigs a weight increasing effective amount of an composition of claim 10.

16. A method of increasing the weight of calves comprising administering to calves a weight increasing effective amount of an composition of claim 10.

17. A method of increasing the weight of poultry comprising administering to poultry a weight increasing effective amount of an composition of claim 1.

18. A method of increasing the weight of poultry comprising administering to poultry a weight increasing effective amount of an composition of claim 10.

19. The method of claim 13 wherein the composition is incorporated into the pigs feed.

20. The method of claim 14 wherein the composition is incorporated into the calves feed.

21. The method of claim 13 wherein the beta adrenergic is orally administered at a daily dose of 10 to 1000 mg/kg of the animal.

22. The method of claim 14 wherein the beta adrenergic is orally administered at an daily dose of 10 to 1000 mg/kg of the animal.

23. The method of claim 15 wherein the beta adrenergic is orally administered at a daily dose of 10 to 1000 mcg/kg of the animal.

24. The method of claim 16 wherein the beta adrenergic is orally administered at a daily dose of 10 to 1000 mcg/kg of the animal.

* * * * *